United States Patent [19]

Ebner et al.

[11] Patent Number: 5,627,125
[45] Date of Patent: May 6, 1997

[54] PROCESS FOR PREPARING CARBOXYLIC ACID SALTS AND METHODS FOR MAKING SUCH CATALYSTS AND CATALYSTS USEFUL IN SUCH PROCESS

[75] Inventors: Jerry R. Ebner, St. Peters; Thaddeus S. Franczyk, Maryland Heights, both of Mo.

[73] Assignee: Monsanto Company, St. Louis, Mo.

[21] Appl. No.: 454,757

[22] Filed: May 31, 1995

Related U.S. Application Data

[60] Division of Ser. No. 407,723, Mar. 20, 1995, which is a continuation-in-part of Ser. No. 269,718, Jul. 1, 1994.

[51] Int. Cl.$^6$ .................................................. B01J 23/72
[52] U.S. Cl. ........................... 502/331; 502/325; 502/330
[58] Field of Search ................................... 502/313, 345, 502/325, 328, 330, 331, 344

[56] References Cited

U.S. PATENT DOCUMENTS

| | | |
|---|---|---|
| H1193 | 6/1993 | Barta et al. . |
| 2,384,817 | 9/1945 | Chitwood . |
| 3,449,413 | 6/1969 | Hartel et al. . |
| 4,321,285 | 3/1982 | Feldstein . |
| 4,547,324 | 10/1985 | Wong et al. . |
| 4,782,183 | 11/1988 | Goto et al. . |
| 4,810,426 | 3/1989 | Fields, Jr. et al. . |
| 5,068,404 | 11/1991 | Miller et al. . |
| 5,292,936 | 3/1994 | Franczyk . |

FOREIGN PATENT DOCUMENTS

| | | |
|---|---|---|
| 513396 | 11/1992 | European Pat. Off. . |
| 0513396A1 | 11/1992 | European Pat. Off. . |
| 61-101250 | 5/1986 | Japan . |
| 6-7679 | 1/1994 | Japan . |

OTHER PUBLICATIONS

Chang et al., "Dependence of selectivity on the preparation method of copper/α-alumina catalysts in the dehydrogenation of cyclohexanol," *Applied Catalysis A: General*, vol. 103, pp. 233–242 (1993).

Barnes, et al., "A Thermoanalytical Study of the Formation and Activation of Novel Copper–Carbon Catalysts," *Journal of Thermal Analysis* (1994), vol. 41, pp. 621–634.

Chang, et al., "Catalytic Activities of Electroless Plated Cu/Alumina Catalysts for the Dehydrogenation of Cyclohexanol," *Journal of Molecular Catalysis* (1994), vol. 88, pp. 223–238.

*Primary Examiner*—Glenn A. Caldarola
*Assistant Examiner*—Alexander G. Ghyka
*Attorney, Agent, or Firm*—Stanley M. Tarter; Grace L. Bonner; Arnold, White & Durkee

[57] ABSTRACT

A process to manufacture a carboxylic acid salt is disclosed wherein an aqueous solution of a primary alcohol is contacted with a base hydroxide in the presence of an effective amount of a catalyst consisting essentially of an alkali resistant support, from about 0.05 wt. % to about 10 wt. %, based on the total weight of the catalyst, of an anchor metal is selected from the group consisting of platinum, palladium, ruthenium, and gold, and between about 1 wt. % and about 50 wt. %, based on the total weight of the catalyst, of an element selected from the group consisting of copper, cobalt, nickel, and cadmium combined with the anchor metal.

39 Claims, 1 Drawing Sheet

PROCESS FOR PREPARING CARBOXYLIC ACID SALTS AND METHODS FOR MAKING SUCH CATALYSTS AND CATALYSTS USEFUL IN SUCH PROCESS

This application is a divisional application of U.S. Ser. No. 08/407,723 filed Mar. 20, 1995, now pending, which is a Continuation-in-Part application of U.S. Ser. No. 08/269,718 filed Jul. 1, 1994, now pending.

BACKGROUND OF THE INVENTION

This invention relates to the preparation of carboxylic acid salts, and more particularly, relates to a method for the preparation of carboxylic acid salts by the reaction of primary alcohols with a hydroxide base in the presence of a novel catalyst. The invention also relates to the preparation of the catalyst and compositions thereof.

Carboxylic acid salts are useful in various applications. The salts can be neutralized to the corresponding acids which are also useful in a number of applications, such as a material for pharmaceuticals, agricultural chemicals, pesticides and the like or precursors thereof. Many of such carboxylic acids are available commercially in large quantities.

U.S. Pat. No. 4,782,183 to Goto et al. discloses a method for the manufacture of amino carboxylic acid salts which comprises contacting an amino alcohol with an alkali metal hydroxide in the presence of a Raney copper catalyst, or a copper catalyst supported on zirconium oxide.

U.S. Pat. No. 4,810,426 to Fields et al. discloses a process for the production of N-phosphonomethylglycine by oxidizing N-phosphonomethylethanolamine, or the cyclic internal ester thereof, with an excess of an aqueous alkali and in the presence of a copper catalyst, and thereafter, heating at a temperature between 200° C. and 300° C. The resulting salt is neutralized with an acid to produce the desired N-phosphonomethylglycine.

U.S. Pat. No. 5,292,936 to Franczyk discloses an improved process to prepare an amino carboxylic acid salt. According to the process, an aqueous solution of an amino alcohol is contacted with an alkali metal hydroxide in the presence of an effective amount of a Raney copper catalyst that has from about 50 parts per million to about 10,000 parts per million of an element selected from the group consisting of chromium, titanium, niobium, tantalum, zirconium, vanadian, molybdenum, manganese, tungsten, cobalt, nickel and mixtures thereof.

Although satisfactory results are achieved by the processes of the prior art to convert an alcohol to a carboxylate using a copper catalyst, or even a Raney copper catalyst, it has now been found, in accordance with the teachings of the present invention, that the novel catalysts of the present invention can be used to convert an alcohol to the corresponding acid salt in a shorter period of time than with the use of other copper catalysts, including Raney copper catalysts. This results in significant capital savings and operating costs, when such reactions are practiced on a commercial scale.

The journal article "Dependence of Selectivity on the Preparation Method of Copper/α-Alumina Catalysts in the Dehydrogenation of Cyclohexanol" by Hsin-Fu Chang et al., *Applied Catalysis A: General*, 103 (1993) 233–242 discloses an electroless copper plating method, a precipitation method and an impregnation method in the preparation of eleven copper/α-alumina catalysts. The effects of the method of preparation on the dehydrogenation reaction of cyclohexanol were investigated. The reported results showed that the dehydrogenation activity increased as the copper loading increased up to a certain limit, and then declined with further copper loading.

SUMMARY OF THE INVENTION

The present invention provides a new and useful process for manufacturing a carboxylic acid salt which comprises contacting a primary alcohol in the presence of water with a strong hydroxide base, such as of an alkali metal hydroxide, an alkaline earth metal hydroxide, a tetraalkyl ammonium hydroxide, and the like, in the presence of an effective amount of a catalyst suspended in the water. The catalyst comprises a hydroxide-resistant support, from about 0.05 weight percent to about 10 weight percent, based on the total weight of the catalyst, of a finely divided anchor metal, such as a precious metal deposited or embedded on the support, between about 1 weight percent and about 50 weight percent, based on the total weight of the catalyst, of a metal selected from the group of copper, cobalt, nickel, cadmium and mixtures thereof in the elementary state which has been electrolessly plated on at least some of on the anchor metal particles. It is to be understood that the term "electroless plating" as used herein means the chemical deposition of an adherent metal coating on a suitable substrate in the absence of an externally applied electric source.

This invention also relates to a catalyst useful for preparing carboxylic acid salts comprising a hydroxide-resistant support, such as carbon, preferably activated carbon, from about 0.05 weight percent to about 10 weight percent, based on the total weight of the catalyst, of an anchor metal in particulate form, preferably selected from the group of metals of platinum, palladium, ruthenium, gold, and mixtures thereof deposited or embedded on the support, and between about 1 weight percent and about 50 weight percent, based on the total weight of the catalyst, of an element selected from the group of copper, cobalt, nickel, cadmium, and mixtures thereof electrolessly plated on at least some of the anchor metal particles. The catalyst is prepared by a method which comprises depositing from about 1 weight percent to about 50 weight percent, based on the total weight of the catalyst, of an element selected from the group of copper, cobalt, nickel, cadmium and mixtures thereof, on a hydroxide-resistant support having from about 0.05 weight percent to about 10 weight percent of an anchor metal selected from the group of platinum, palladium, ruthenium, gold and mixtures thereof.

Also, in accordance with the present invention there is provided a new and useful method for preparing a catalyst by electrolessly plating of an element selected from the group comprising copper, cobalt, nickel, cadmium, and mixtures thereof. The method comprises the steps of mixing together in water a source of water soluble ions of said plating metal, a suitable complexing agent, and an alkali resistant support carrying embedded particles of an anchor metal and thereafter slowly adding a reducing agent to the resulting mixture to reduce the said ions to elemental form, whereby the metal resulting from the reduction is electrolessly plated on at least some of the nonembedded surface of the anchor metal.

DESCRIPTION OF DRAWING

In the attached drawing

DETAILED DESCRIPTION OF THE INVENTION

Figure 1:
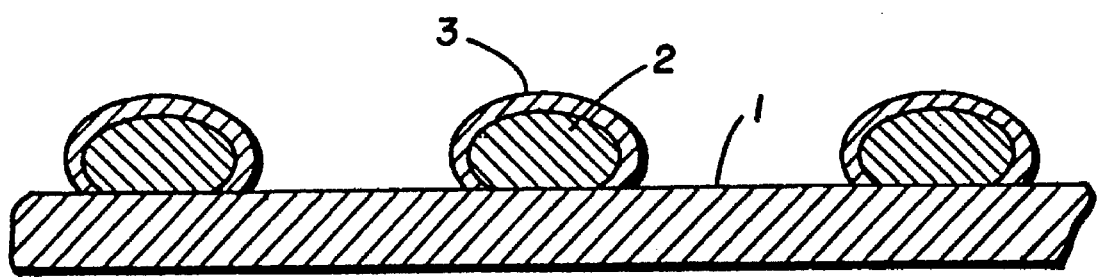
FIG. 1 is a greatly magnified cross-sectional representation of the novel catalyst of the invention. Reference numeral 1 denotes an alkali resistant support on which particles of an anchor metal 2 are partially embedded. The nonembedded surface of the anchor metal is coated with an electroless plating 3 of a catalytically active nonprecious metal in the elementary state.

The primary alcohols which are useful as starting materials in the process of the present invention can be monohydric or polyhydric aliphatic, cyclic or aromatic compounds, including polyether glycols, which react with a strong base to form a carboxylate. It is necessary that the alcohol and the resulting carboxylate are stable in a strongly basic solution, and that the alcohol is at least somewhat water soluble.

Suitable primary monohydric alcohols include aliphatic alcohols which can be branched, straight chain, or cyclic and aromatic alcohols, such as benzyl alcohol and can be substituted with various nonhindering groups, provided that the subtituent groups do not adversely react with a strong base, the hydroxide resistant support, or the catalyst at the temperatures and pressure used for the conversion of the alcohol to the acid. Suitable aliphatic alcohols include ethanol, propanol, butanol, pentanol, and the like.

Amino alcohols represented by the formula

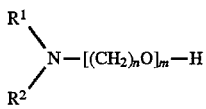

are also useful as starting materials in the present process where n is an integer from 2 to 10 or more and m is at least 1 and can be as high as 50 or more. When $R^1$ and $R^2$ are both hydrogen and n is 2, the amino alcohol is monoethanolamine. When one of $R^1$ and $R^2$ is —$CH_2CH_2OH$ or —$CH_2COOH$, and the other R group is hydrogen and n is 2, the resulting product from the amino alcohol is an iminodiacetate salt. When both $R^1$ and $R^2$ are —$CH_2CH_2OH$ or —$CH_2COOH$, the resulting product from the amino alcohol would be a nitrilotriacetate salt. Specific amino alcohols include, for example, monoethanolamine, diethanolamine, triethanolamine, N-methyethanolamine, N-ethylethanolamine, N-isopropylethanolamine, N-butylethanolamine, N-nonylethanolamine, N-(2-aminoethyl)ethanolamine, N-(3-aminopropyl)ethanolamine, N,N-dimethylethanolamine, N,N-diethylethanolamine, N,N-dibutylethanolamine, N-methyldiethanolamine, N-ethyldiethanolamine, N-propyldiethanolamine, N-butyldiethanolamine, N-methyl-N-(3-aminopropyl) ethanolamine and 3-aminopropanol.

In the above formula, $R^1$ and/or $R^2$ can also be an alkyl group having from 1 to 6 carbon atoms, for example, methyl, ethyl, propyl, isopropyl, butyl, isobutyl and the like. By the practice of the present invention there are then provided corresponding amino acid salts with these alkyl groups which are useful in a number of applications. $R^1$ or $R^2$ can also be a phosphonomethyl group such that the starting amino acid can be N-phosphonomethylethanolamine, and the resulting amino acid salt can be the salt of N-phosphonomethylglycine. When one of $R^1$ or $R^2$ is phosphonomethyl and the other is —$CH_2CH_2OH$, the resulting amino acid salt is the salt of N-phosphonomethyliminodiacetic acid, which can be converted to N-phosphonomethylglycine by a number of techniques known to those skilled in the art. When one of $R^1$ or $R^2$ is phosphonomethyl, and the other is lower alkyl group, the resulting amino acid salt is N-alkyl-N-phosphonomethylglycinate which can be converted to N-phosphonomethylglycine by the teachings in U.S. Pat. No. 5,068,404 to Miller and Balthazor.

Another aspect of the present invention is the use of the catalyst of the present invention, wherein the amino alcohol to be dehydrogenated to the corresponding carboxylic acid salt is a compound having the formula

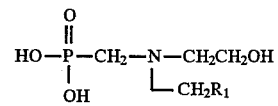

wherein $R_1$ is $C_4$–$C_7$ aryl, preferably phenyl or substituted phenyl, and the resulting carboxylic acid salt is an alkali metal salt of N-phosphonomethylglycine.

The amount of catalyst to be used for converting the alcohol to the corresponding acid can range between about 1 weight percent and about 70 weight percent, preferably 1 to 40 weight percent, based on the amount of the starting alcohol. It has been found that the catalyst of the present invention can generally be used repeatedly in the reaction for a greater number of times than a conventional Raney copper catalyst.

The hydroxide bases suitable for use in the process of the present invention include the alkaline earth metal hydroxides, such as magnesium hydroxide, calcium hydroxide, barium hydroxide and the like. The hydroxide base can also be a tetraalkyl ammonium hydroxide having up to and including 5 carbon atoms in each alkyl group, such as tetramethyl ammonium hydroxide, dimethyldipropyl ammonium hydroxide, tributylethyl ammonium hydroxide and the like or other strong organic bases, such as quanidine and aminoquanidine. However, alkali metal hydroxides are preferred. Suitable alkali metal hydroxides for use in the process of the present invention include lithium hydroxide, sodium hydroxide, potassium hydroxide, rubidium hydroxide and cesium hydroxide. Because of their ready availability and ease of handling, sodium hydroxide and potassium hydroxide are preferred; and sodium hydroxide is especially preferred. The amount of the hydroxide base to be used is an equivalent amount in the range of 1.0 to 2.0 equivalents relative to the hydroxyl group of the alcohol to be used in the reaction, as determined after neutralization of any acid functional groups and/or hydrolysis of any ester functional groups of the amino alcohol starting material. The hydroxide can be in the form of flakes, powder, pellets or an aqueous solution.

In the process of the present invention, it is only necessary to contact the alcohol with an alkali metal hydroxide in a reaction vessel in the presence of the catalyst of the present invention at a temperature between about 70° C. and 250° C., preferably between about 100° C. and about 190° C. and more preferably between about 140° C. and 180° C. At temperatures above about 220° C., the catalyst generally begins to lose some selectivity. At temperatures below about 50° C., satisfactory results may be obtained, but the reaction may be undesirably slow. Generally speaking, the reaction of polyetherglycols to produce the corresponding carboxylic acid salts will require a more elevated temperature.

Pressure in excess of atmospheric pressure is normally but not always required for the reaction to proceed at a sutiable rate at the temperatures indicated above. However, the reaction pressure is desired to be as low as possible to provide adequately high reaction velocity. Generally, it is necessary to exceed the minimum pressure at which the reaction proceeds in the liquid phase, preferably between about $1.96 \times 10^5$ Pascals and about $2.94 \times 10^6$ Pascals, preferably in the range of about $4.90 \times 10^5$ Pascals and about $1.96 \times 10^6$ Pascals. The conversion of the alcohol to the corresponding acid salt proceeds with the liberation of hydrogen, which is vented with care from the pressurized reaction vessel. The venting may be monitored to determine the rate and completeness of the reaction.

As is well-known in the art, electroless metal plating results in the absence of an externally applied electric current by using an aqueous plating bath or aqueous deposition solution of a water soluble salt of the metal to be deposited. The preferred metal is copper which is present in the plating bath as a water soluble salt, such as copper (cuptic) sulfate and the like. Other conventional ingredients in the bath include a reducing agent, an alkaline hydroxide, a complexing or chelating agent, and optionally other formulation additives, such as stabilizers, surfactants, brightness and wetting agents, etc.

The choice of which specific bath composition to use is predicated upon several factors well known in the art.

The preferred reducing agent for copper deposition is formaldehyde or other substance reducible to the $XCOO^-$ ion, wherein X is hydrogen for formaldehyde and $CH_3$ for acetaldehyde. For electroless reduction of nickel suitable reducing agents include, for example, sodium hypophosphite, sodium borohydride, dimethylamine borane (DMAB) and hydrazinc.

Suitable chelating agents or complexing agents include the Rochelle salts (tartrates), ethylenediaminetetraacetic acid (EDTA), N-hydroxyethylethylenediamine triacetic acid (HEEDTA), nitrilotriacetic acid (NTA), N,N,N',N'-tetrakis (2-hydroxypropyl)ethylenediamine (Quadrol chelant) or other substances to insure keeping the metal ion suitably soluble in the electroless metal bath.

Particles of the anchor metal to be coated are embedded on the surface of an alkali-resistant support to form a substrate. Finely-divided particles of platinum embedded on a carbon support are preferred. The substrate is contacted under suitably selected conditions of pressure, temperature and time for the best deposition of the chelated metal onto the anchor metal and sometimes as free standing metal particles attached to the substrate. Suitable temperatures range from the freezing point of the deposition solution to the reflux temperature. The thickness of the metal plating is selected so as to give a catalytic surface. In general, the thickness of the base metal coating on the plated anchor metal particles is about 0.3 to 500 nanometers, preferably 1 to 5 nanometers.

Surfactants may also be employed in the electroless plating bath. Suitable surfactants are substances which are capable of lowering the surface tension of a liquid or the interfacial tension between a liquid and solid. Such substances possess the common feature of a water soluble (hydrophilic) moiety attached to an organic (hydrophobic) moiety and include detergents and emulsifiers.

Hydroxide-resistant supports in the catalyst are necessary since the reaction to convert the alcohol to the corresponding acid salt is conducted in a strong basic solution. Suitable supports include titanium oxide, zirconium oxide and carbon. Of these carbon is preferred. Activated carbon is even more preferred.

The particulate anchor metal deposited on the hydroxide-resistant support can be a noble metal. By noble metal is meant gold, platinum, palladium ruthenium or mixtures thereof. Of these platinum is preferred. The amount of anchor metal to be deposited on the hydroxide-resistant support can vary from about 0.05 weight percent to about 10 weight percent, based on the total weight of the catalyst. When less than about 0.05 weight percent anchor metal is deposited on the hydroxide-resistant support, there is insufficient anchor metal to combine with the copper, cobalt, nickel, and/or cadmium to provide a satisfactory catalyst for many reactions. On the other hand, when more than about 10 weight percent anchor metal, based on the total weight of the catalyst is deposited on the support, the crystallite size of plated metal tends to increase. Larger crystal sizes of the plated elemental metal sometimes leads to reduced catalytic performance. It is preferred to use from about 0.1 weight percent to about 5 weight percent, based on the total weight of the catalyst, of the anchor metal.

Suitable hydroxide-resistant supports containing a suitable anchor metal can be obtained commercially.

The catalyst of the present invention is prepared by depositing from about 1 weight percent to about 50 weight percent, based on the total weight of the catalyst, of an element selected from the group consisting of copper, cobalt, nickel, cadmium and mixtures thereof on a hydroxide-resistant support having from about 0.05 weight percent to about 10 weight percent of an anchor metal preferably selected from the group consisting of platinum, palladium, ruthenium, gold and mixtures thereof. The amount of deposited element (i.e., copper, cobalt, nickel and/or cadmium) should be sufficient to cover at least some of the embedded particles. Silver may be deposited on the anchor metal where the anchor metal is not silver. In addition to the coated particles the presence of at least some particles of the plating metal embedded on the support but not adherent on the anchor metal can exist.

X-ray Photoelectron Spectroscopy (XPS) is a technique which can be used to measure the relative concentration of deposited surface atoms in the catalyst. Using this technique, it has been found that preferably in the catalysts of this invention the XPS surface atomic ratio of the deposited metal on the anchor metal is greater than 2.0, and more preferably, the XPS surface atomic ratio is greater than the corresponding bulk atomic ratio.

Any number of techniques can be used to deposit the anchor metal on the alkali resistant substrate and to deposit the copper, cobalt, nickel, and/or cadmium onto the anchor metal. It is preferred, however, to use electroless metal deposition. A stated above electroless metal deposition refers to the chemical deposition of an adherent metal coating on a suitable substrate in the absence of an externally applied electric source.

Regardless of the method of depositing the anchor metal onto the substrate, the size of the anchor metal particles is an important parameter in that the size influences the size of the crystals of copper, cobalt, nickel, and/or cadmium to be deposited. The average crystallite size of the copper, cobalt, nickel, cadmium or mixtures thereof should be less than about 500 Angstroms; and in the case of copper, it is preferred that the average crystallite size is less than about 300 Angstroms. Although applicants do not wish to be bound by any particular theory, it is believed that a uniform distribution of the anchor metal is best for achieving high reaction yields, but not necessary for achieving fast reaction rates. Further, it is believed that it is important to have small, well-reduced, highly-dispersed anchor metal particles.

In practice, the substrate containing the anchor metal is added to and slurried in water. Next, a plating solution, e.g., copper plating solution, is prepared by mixing the plating solution in the appropriate proportions while the slurry of substrate and water is gently stirred at a temperature of about 0° C. up to 30° C. or higher in an open container. The plating solution containing a complexing agent and a reducing agent is added to the slurry in small increments by monitoring the pH with each addition. After an appropriate time interval, the next increment of the slurry is slowly added. The amount of plating solution added depends on the desired weight percent catalytic element on the anchor metal of the catalyst. When the deposition of catalytic element is complete, an essentially colorless filtrate results.

The resulting aqueous solution in one embodiment of the invention comprises the following active ingredients.

| Copper sulfate | 4.0 g/L |
| Formaldehyde | 6.0 g/L |
| Sodium hydroxide | 9.0 g/L |
| Excess EDTA chelant | 0.06 molar |

Next, the finished catalyst is filtered and washed with distilled water. The filtration is best done in an inert atmosphere, such as a nitrogen blanket, to avoid exposure of the catalyst to air. Washing the catalyst removes unreacted components such as parts per million impurities and unreacted reducing agent, such as formaldehyde. It has been found that from about 0.5 to 1.5 weight percent alkali metal normally is left on the catalyst, which is usually not harmful. The catalyst should be stored in a manner which avoids exposure to oxygen, preferably by being kept under water.

The invention is further illustrated by but not limited to the following examples.

As indicated above the preferred method for preparing the catalyst of the present invention comprises the steps of first stirring or mixing together in water a source of water soluble metal ions, such as copper ions, a suitable complexing agent, and an alkali resistant support carrying embedded particle of an anchor metal and thereafter slowly adding, such as by dropwise addition, a reducing agent, such as formaldehyde, hydrazine or the like to the stirred mixture. The metal ions are reduced to elemental metal form and the metal resulting from the reduction is electrolessly plated on at least some of the nonembedded surface of the anchor metal. Some of the reduced metal may be deposited as free standing metal particles on the support without being deposited on the anchor metal.

EXAMPLE 1

This example illustrates the preparation of a catalyst of the present invention.

Into a one-liter glass beaker containing a Teflon polymer coated, 5 centimeter long, magnetic stirring bar, on a magnetic stirring plate are added 169 mL distilled water and 5 weight percent platinum on activated carbon in powder form, available from Degussa Corporation of Ridgefield Park, N.J., which corresponds to 13.37 grams on a dry weight basis. In a separate one-liter beaker a copper plating solution is prepared by adding the following components, most of which are available from MacDermid, Inc. of Waterbury, Conn., with stirring in the following order:

(1) 687 ml deionized water
(2) 90 ml MACuPlex Ultra Dep 1000B*
(3) 54 ml MACuPlex Ultra Dep 1000A*
(4) 18 ml MACuPlex Ultra Dep 1000D*
(5) 5 ml 37% w/w formaldehyde
* proprietary products of MacDermid TOTAL VOLUME 854 ml According to MacDermid's product description for Product Code No. 17970, the resulting aqueous solution comprises the following active ingredients:

| Copper sulfate | 4.0 g/L |
| Formaldehyde | 6.0 g/L |
| Sodium hydroxide | 9.0 g/L |
| Excess EDTA chelant | 0.06 molar |

The resulting plating solution is filtered and then added to the stirred slurry of the 5 percent platinum on activated carbon by adding 122 milliliter increments every 3 minutes at 40° C. The pH is monitored to verify the extent of the reaction. Time between additions is extended when gas evolution becomes too vigorous.

After the addition of the plating solution is completed, the catalyst is recovered by filtration using a 4-liter vacuum flask, a 350 ml coarse glass filter funnel, and a glass dome over the top of the funnel purged with nitrogen. After filtration, the solid material is washed with three to four 250-ml portions of deionized water. The dry weight yield of catalyst in this preparation is 18.4 grams. Microanalysis of the catalyst shows the elemental composition to be 13.4 weight percent copper and 3.4 weight percent platinum, based on the total weight of the catalyst. The average copper crystal size as determined by XRD line broadening is found to be 157 Angstroms.

EXAMPLE 2

This example shows another preparation of a catalyst of the present invention.

To a 2-liter glass beaker containing a Teflon polymer coated, 2.5 centimeter long, magnetic stirring bar on a magnetic stir plate is added distilled water (190 ml) followed by 5 weight percent platinum on activated carbon, available from Degussa Corporation, corresponding to 16.42 grams (dry weight). An aqueous copper plating solution is prepared in a 4-liter beaker by adding the following components with stirring.

(1) 500 ml DI water
(2) $NaKC_4H_4O_6 \cdot 4H_2O$ (tartrate) [29.99 g, 0.106 mole]; stir to dissolve
(3) In a separate beaker, dissolve 11.79 gms of $CuSO_4 \cdot 5H_2O$ (3 gms Cu,) (0.047 mol) in 400 ml deionized water
(4) Add copper solution (3) to the resulting tartrate solution (2)
(5) Add 13.60 grams of 50 weight percent NaOH (0.17 mol)
(6) 11.35 ml 37 weight percent formaldehyde (0.15 mol)

TOTAL VOLUME 1125 ml

The resulting plating solution is added to the slurry of 5 weight percent platinum on carbon in a total of about twelve, 79 ml increments with each increment being separately added every 2.5 minutes. The pH is monitored to verify the extent of the reaction and to delay incremental addition in time if and when the solution degassing becomes too vigorous. The catalyst, after the plating solution is added to the slurry, is recovered by filtration as in Example 1. The dry weight yield is 20.03 grams. The composition is analyzed and is found to be 14.5 percent copper and 3.8 percent platinum, based on the total weight of the catalyst. The average copper crystal dimension is 119 Angstroms.

EXAMPLE 3

Example 2 is repeated except that components (1) through (5) are mixed together with the platinum on carbon substrate; and thereafter formaldehyde is added dropwise to the resulting mixture over a 30 minute period. As a result improved deposition of the copper onto the platinum is obtained as compared using the catalyst composition prepared in accordance with the method of Example 2. The catalyst is evaluated in the conversion of diethanolamine to the corresponding acid salt. The reaction results in a yield of the corresponding acid salt of greater than 95 percent.

EXAMPLE 4

This example illustrates the conversion of diethanolamine to the disodium salt of iminodiacetic acid (DSIDA) using the catalyst of Example 1.

Into a 300 ml autoclave equipped with a stirrer and a 0.5 micron filter mounted at the bottom of the autoclave are charged 15 grams of the catalyst of Example I under an argon atmosphere, a 50% sodium hydroxide solution (61.5 g, 0.77 mol), an aqueous solution of diethanolamine (78.9 weight percent, 0.36 mol) and distilled water (47.5 g). The autoclave is rapidly heated to the desired reaction temperature while maintaining the pressure at $1.03 \times 10^6$ Pascals with stirring being accomplished at about 800 revolutions per minute. The reaction is monitored by measuring the hydrogen off gas from the reaction. After the reaction is completed, the autoclave is cooled to room temperature. The resulting reaction mixture is discharged through the bottom of the autoclave through the filter and collected. Distilled water is then added to the autoclave, and the catalyst is stirred with the water which is then also discharged through the bottom of the autoclave. About 100 ml to 200 ml of water is used. While the autoclave is maintained under a nitrogen blanket, reactants are recharged (excluding the catalyst) and an identical run is made as above. The results of nine cycles are shown in Table 1.

TABLE 1

| Cycle | Temp. (°C.) | Reaction Time (Minutes) | DSIDA Yield (%) |
|---|---|---|---|
| 1 | 161 | 103 | 94.5 |
| 2 | 161 | 106 | 94.8 |
| 3 | 155 | 132 | 95.1 |
| 4 | 155 | 138 | 95.0 |
| 5 | 155 | 144 | 94.9 |
| 6 | 155 | 144 | 94.9 |
| 7 | 155 | 147 | 94.9 |
| 8 | 155 | 150 | 94.8 |
| 9 | 156 | 150 | 94.7 |

EXAMPLE 5

This example illustrates the conversion of diethanolamine to the disodium salt of iminodiacetic acid using the catalyst of Example 2.

The procedure of Example 4 is repeated except that the catalyst of Example 2 is used instead of the catalyst of Example 1. The results are shown in Table 2.

TABLE 2

| Cycle | Temp. (°C.) | Reaction Time (Minutes) | DSIDA Yield (%) |
|---|---|---|---|
| 1 | 156 | 61 | 95.2 |
| 2 | 151 | 94 | 95.7 |
| 3 | 151 | 97 | 95.6 |
| 4 | 151 | 96 | 95.8 |
| 5 | 144 | 147 | 95.4 |
| 6 | 144 | ND* | ND* |
| 7 | 145 | 154 | 95.5 |
| 8 | 145 | 155 | 95.4 |

*ND - not determined

EXAMPLE 6

This example illustrates the preparation of another catalyst of the present invention and its use.

Into a 4-liter glass beaker containing Teflon polymer coated, 5-centimeter long, magnetic stirring bar, on a magnetic stirring plate are added distilled water (471 ml) and wet 3 weight percent palladium on activated carbon which corresponds to 40.5 grams of 3 weight percent palladium on activated carbon on a dry weight basis. In a separate 4-liter beaker a copper plating solution is prepared by adding the following components with stirring in the following order:

(1) 1918.6 ml dionized water (2) 251.2 ml MACuPlex Ultra Dep 1000B (3) 150.73 ml MACuPlex Ultra Dep 1000A (4) 50.24 ml MACuPlex Ultra Dep 1000D (5) 13.96 ml 37 percent by weight formaldehyde TOTAL VOLUME 2384.8 ml This plating solution is added to the slurry of the 3 weight percent palladium on activated carbon, available from Engelhard Corporation of Iselin, N.J., by adding 200 milliliter increments every 2.5 minutes. The pH is monitored to verify the extent of the reaction. Time between incremental additions is extended, when gas evolution becomes too vigorous.

After the plating solution is added, the catalyst is recovered by filtration using a 4-liter vacuum flask, a 500 ml coarse glass filter funnel, and a glass dome over the top of the funnel purged with nitrogen. After filtration, the solid material is washed with three to four 250 milliliter portions of deionized water. The dry weight yield in this preparation is 54.27 grams and microanalysis of the catalyst shows the elemental composition to be 13.5 weight percent copper and 2.1 weight percent palladium, based on the total weight of the catalyst. The average copper crystal size as determined by XRD line broadening is 127 Angstroms.

The procedure of Example 4 is repeated except that the above catalyst is used. The results are shown in Table 3.

TABLE 3

| Cycle | Temp. (°C.) | Reaction Time (Minutes) | DSIDA Yield (%) |
|---|---|---|---|
| 1 | 160.5 | 120 | 94.9 |
| 2 | 161.5 | 105 | 96.1 |
| 3 | 161 | 95 | 95.2 |
| 4 | 161 | 97 | 95.1 |
| 5 | 156.5 | 121 | 96.3 |
| 6 | 151.5–161.5 | 129 | 96.3 |

TABLE 3-continued

| Cycle | Temp. (°C.) | Reaction Time (Minutes) | DSIDA Yield (%) |
| --- | --- | --- | --- |
| 7 | 156 | 128 | 96.3 |
| 8 | 156 | 120 | 96.3 |
| 9 | 156 | 121 | 96.3 |
| 10 | 156 | 122 | 96.2 |

EXAMPLE 7

This example illustrates the use of the present catalyst to convert N-(2-hydroxyethyl)aminomethylphosphonic acid to N-phosphonomethylglycine. Into a 300 ml nickel autoclave equipped with a stirrer is charged with a mixture of N-(2-hydroxyethyl)aminomethylphosphonic acid (12.0 g, 0.077 mol), water (120 g), 50 weight percent sodium hydroxide (21.7 g, 0.271 mol), and 12.5 g of the catalyst of Example 2. The autoclave is sealed and heated to 150° C. under pressure to $9.32 \times 10^5$ Pascals while stirring the liquid phase in the autoclave until hydrogen evolution essentially ceases. The yield of N-phosphonomethylglycine as its sodium salt was 94 weight percent.

EXAMPLE 8

This example illustrates the conversion of 2-oxo-3-oxazolidinylmethylphosphonic acid to N-phosphonomethylglycine in salt form using the present catalyst.

The procedure of Example 7 is repeated except that N-phosphonomethyl-2-oxazolidone made by the process described in U.S. Pat. No. 4,547,324 is used instead of N-2-(hydroxyethyl)aminomethylphosphonic acid. After hydrogen evolution ceases, the yield of N-phosphonomethylglycine is 86 weight percent as determined by HPLC analysis.

EXAMPLE 9

This example illustrates the use of the copper catalyst of Example 2 to convert 3-aminopropanol to sodium 3-aminopropionate.

The mixture consisting of 3-aminopropanol, (49.8 g, 0.66 mol), a slurry of 12 g of the catalyst of Example 2 in 50 g of water, 50 weight percent NaOH (57 g, 0.7 mol), and 25 g deionized water is charged to a 300 ml nickel Parr reactor equipped with a stirrer, a gas regulator to maintain constant back pressure, and a Porter hydrogen mass flow indicator interfaced with an IBM computer. Heating to 160° C. induces rapid hydrogen evolution, and after it ceases, analysis of the filtered product mixture by NMR is consistent with a 85:15 ratio of sodium 3-aminopropionate and sodium propionate, respectively.

EXAMPLE 10

This example illustrates the use of the present catalyst to convert an aromatic alcohol to the corresponding acid salt.

A mixture containing benzyl alcohol (62.6 g, 0.58 mol), a slurry of 12 g of the catalyst of Example 2 in 50 g of water, 50 weight percent NaOH (50.3 g, 0.63 mol), and 24 g deionized water is charged to the reactor described in Example 7. Heating to 160° C. yields evolution of hydrogen. After 30 minutes the temperature is increased to 170° C. to speed conversion. After hydrogen evolution ceases the filtered reaction mixture is analyzed by NMR. The $^1$H and $^{13}$C NMR spectra obtained from the product is consistent with that of sodium benzoate. An aliquot of the product mixture is acidified with HCl and recrystallized from water to afford white plates: m.p. 121°–122° C. (lit. m.p. 122.4° C.)

EXAMPLE 11

This example illustrates the use of the present catalyst to convert a polyol to the corresponding acid.

The autoclave of Example 7 is charged with ethylene glycol (30.3 g, 0.49 mol), a 12 g of the catalyst of Example 2 in 50 g of water, 50 weight percent NaOH (39.77 g, 0.497 mol), and 70 g of deionized water. The mixture is heated to 160° C. with rapid evolution of hydrogen. After hydrogen evolution ceases, analysis of the filtered reaction mixture by HPLC reveals a 95 weight percent yield consisting of about 90 mol weight percent sodium glycolate and 10 mol percent sodium oxalate.

EXAMPLE 12

This example illustrates the conversion of cinnamyl alcohol to the corresponding acid.

Into a 300 ml nickel autoclave are charged cinnamyl alcohol (50.0 g, 0.37 mo1), sodium hydroxide (34.6 g, 0.43 mol), the catalyst of Example 2 (12.8 g catalyst suspended in 48.6 g water) and water (75 g). The autoclave is sealed and purged with nitrogen. The autoclave is heated under pressure of $1.0 \times 10^6$ Pascals to 170° C. After hydrogen evolution ceases, the reaction product filtered and the basic filtrate is extracted with diethylether. The aqueous phase is acidified and extracted with ether. The acid and base extracts are evaporated and analyzed. The reaction yields sodium 3-phenylpropionate (69 mol percent), 3-phenylpropanol (25 mol percent) and sodium benzoate (8 mol percent).

EXAMPLE 13

This example illustrates the conversion of polytetrahydrofuran (PTHF) to the corresponding acid salt. The polytetrahydrofuran used in this example is a linear chain polymer of the formula $H(OCH_2CH_2CH_2CH_2)_nOH$ with an average molecular weight of about 250.

Into a 300 ml autoclave are charged 15 grams of the catalyst prepared in accordance with Example 2, 35.0 grams of 50 weight percent sodium hydroxide, 37.8 grams of polytetrahydrofuran and 61 grams of deionized water. The contents of the autoclave are rapidly heated to a temperature between 160° C.–170° C. while maintaining the pressure at $1.03 \times 10^6$ Pascals. Slurring is maintained at 800 revolutions per minute. After hydrogen evolution ceases, the reaction product is cooled to 95° C., removed from the autoclave. The autoclave is rinsed with about 150 ml of distilled water. The filtrate and water wash are combined and analyzed for the dibasic acid. The conversion from the diol polymer to the corresponding the diacid salt is essentially quantitative.

EXAMPLE 14

Example 13 is repeated except polyethylene glycol having a molecular weight of about 200 is used instead of polytetrahydrofuran. Eventually 100 percent of the diol is converted to the disodium salt of the corresponding dibasic acid having the chemical formula of $NaOOCCH_2$—$(OCH_2CH_2)_x$—$OCH_2COONa$.

EXAMPLE 15

In this example N-benzyl-N-phosphonomethylaminioethanol is converted to the corresponding alkali metal salt of N-phosphonomethylglycine.

Example 13 is repeated except that 35 grams of N-benzyl-N-phosphonomethylaminoethanol is used instead of PTHF. N-phosphonomethylglycine in a yield of greater than 95 percent is produced.

Although the invention has been described in terms of specified embodiments which are set forth in considerable detail, it should be understood that this is by way of illustration only since alternative embodiments and operating techniques will become apparent to those skilled in the art in view of the disclosure. For example, the copper catalyst of the present invention can be used for any number of other reactions other than the conversion of an alcohol to an acid, for example, hydrogenation reactions and dehydrogenation reactions that are common to copper catalysts. In addition, the electrolessly plated catalysts of the present invention which are nickel, cobalt, cadmium, or mixtures combined with the anchor metal can be used to catalyze those reactions where such metals are commonly used as a catalyst. Accordingly, modifications can be made without departing from the spirit of the described invention.

What is claimed:

1. A supported catalyst useful in the preparation of carboxylic acid salts, said catalyst comprising:
   (a) an alkali resistant support;
   (b) a plurality of noble metal particles dispersed and partially embedded in said support, the non-embedded portion of said particles having non-embedded surfaces, said noble metal on said surfaces being in an elemental state;
   (c) a coating of a catalytically active metal selected from the group of copper, cobalt, nickel, cadmium or mixture thereof, said cataytically active metal being in elemental form, said coating being attached to and covering at least some of the non-embedded surfaces of said noble metal particles, said coating having an outside catalytically active surface.

2. The catalyst of claim 1 wherein the noble metal is platinum, palladium, ruthenium, gold or a mixture thereof.

3. The catalyst of claim 1 wherein the catalytically active metal is copper.

4. The catalyst of claim 1 wherein the support is titanium oxide, zirconium oxide, carbon or activated carbon.

5. The catalyst of claim 1 wherein some particles of the catalytically active metal are embedded on the support.

6. A supported catalyst useful in the preparation of carboxylic acid salts, said catalyst comprising:
   (a) a carbon support;
   (b) finely divided particles of noble metal partially embedded in a carbon support so as to define an embedded portion and a non-embedded portion, the non-embedded portion having a non-embedded surface;
   (c) a coating of copper attached to said noble metal and covering the non-embedded surfaces of at least some of said noble metal particles, said coating of copper metal having an outside surface in elemental state, said outside surface being catalytically active in the preparation of carboxylic acid salts.

7. The catalyst of claims 1 or 6 wherein the noble metal comprises between about 0.05 to about 10 weight percent of the catalyst.

8. The catalyst of claims 1 or 6 wherein said catalyst is in the form of a catalytically active powder.

9. The catalyst of claims 1 or 6 wherein the amount of copper metal is between about 1 to about 50 weight percent of the catalyst.

10. The catalyst of claims 1 or 6 wherein some discrete particles of copper are embedded in the support.

11. The supported catalyst of claim 1 wherein the noble metal particles comprise from about 0.05 weight percent to about 10 weight percent of the supported catalyst.

12. The supported catalyst of claim 1 wherein the noble metal particles comprise from about 0.1 weight percent to about 5 weight percent of the supported catalyst.

13. The supported catalyst of claim 1 wherein the catalytically active metal comprises from about 1 to about 50 weight percent of the supported catalyst.

14. The supported catalyst of claim 11 wherein the catalytically active metal comprises from about 1 to about 50 weight percent of the supported catalyst.

15. The supported catalyst of claim 12, wherein the catalytically active metal comprises from about 1 to about 50 weight percent of the supported catalyst.

16. The supported catalyst of claim 1 wherein the XPS surface atomic ratio of the catalytically active metal to the noble metal is greater than 2.0.

17. The supported catalyst of claim 14 wherein the XPS surface atomic ratio of the catalytically active XPS surface atomic ratio of the catalytically active metal to the noble metal is greater than 2.0.

18. The supported catalyst of claim 15 wherein the XPS surface atomic ratio of the catalytically active metal to the noble metal is greater than 2.0

19. The supported catalyst of claim 1 wherein the XPS surface atomic ratio of the catalytically active metal to the noble metal is greater than the corresponding bulk atomic ratio.

20. The supported catalyst of claim 14 wherein the XPS surface atomic ratio of the catalytically active metal to the noble metal is greater than the corresponding bulk atomic ratio.

21. The supported catalyst of claim 15 wherein the XPS surface atomic ratio of the catalytically active metal to the noble metal is greater than the corresponding bulk atomic ratio.

22. The supported catalyst of claim 1 wherein the average crystallite size of the catalytically active metal is less than about 500 Angstroms.

23. The supported catalyst of claim 6 wherein the average crystallite size of copper is less than about 300 Angstroms.

24. The supported catalyst of claim 14 wherein the average crystallite size of the catalytically active metal is less than 500 Angstroms.

25. The supported catalyst of claim 15 wherein the catalytically active metal is copper and the average crystallite size of copper is less than about 300 Angstoms.

26. The supported catalyst of claim 21 wherein the catalytically active metal is copper and the average crystallite size of copper is less than about 300 Angstoms.

27. The supported catalyst of claim 1 wherein the coating defines a layer and the thickness of the layer is from about 0.3 to 500 nanometers.

28. The support catalyst of claim 1 wherein the coating defines a layer and the thickness of the layer is from 1 to 5 nanometers.

29. The supported catalyst of claim 14 wherein the coating defines a layer and the thickness of the layer is from about 0.3 to 500 nanometers.

30. The supported catalyst of claim 14 wherein the coating defines a layer and the thickness of the layer is from about 1 to 5 nanometers.

31. The supported catalyst of claim 15 wherein the coating defines a layer and the thickness of the layer is from about 0.3 to 500 nanometers.

32. The supported catalyst of claim 15 wherein the coating defines a layer and the thickness of the layer is from about 1 to 5 nanometers.

33. The supported catalyst of claim 21 wherein the coating defines a layer and the thickness of the layer is from about 1 to 5 nanometers.

34. The supported catalyst of claim 1 wherein said outside catalytically active surface is free of an alloy of the noble metal with the catalytically active metal.

35. The supported catalyst of claim 6 wherein said outside catalytically active surface is free of an alloy of the noble metal with the catalytically active metal.

36. The supported catalyst of claim 33 wherein said outside catalytically active surface is free of an alloy of the noble metal with the catalytically active metal.

37. A supported catalyst useful in the preparation of carboxylic acid salts, said catalyst consisting essentially of:

(a) an alkali resistant support;

(b) a plurality of noble metal particles dispersed and partially embedded in said support, the non-embedded portions of said particles having non-embedded surfaces, said noble metal as said surfaces being in elemental form;

(c) a coating of a base metal selected from the group of copper, cobalt, nickel, cadmium, or mixtures thereof, said base metal being in elemental form, said coating being attached to and covering at least some of the non-embedded surfaces of said noble metal particles, said coating having an outside catalytically active surface.

38. The catalyst of claims 1 or 6 wherein the thickness of plated metal is about 0.3 to 500 nanometers.

39. The catalyst of claims 1 or 6 wherein the thickness of plated metal is about 1 to 5 nanometers.

* * * * *

UNITED STATES PATENT AND TRADEMARK OFFICE
CERTIFICATE OF CORRECTION

PATENT NO. : 5,627,125
DATED : May 6, 1997
INVENTOR(S) : Jerry R. Ebner and Thaddeus S. Franczyk It is certified that error appears in the above-identified patent and that said Letters Patent is hereby corrected as shown below:

Title page, item [54] and col. 1, delete the first occurrence of "PROCESS" and insert therefor--CATALYSTS--.

Title page, item [54] and col. 1, delete "AND CATALYSTS USEFUL IN SUCH PROCESS".

In claim 1, column 13, line 33, delete "cataytically" and insert therefor --catalytically--.

In claim 17, column 14, lines 21-22, please delete the second occurrence of "XPS surface atomic ratio of the catalytically active".

In claim 25, column 14, line 49, and in claim 26, column 14, line 52, delete "Angstoms" and insert therefor --Angstroms--.

In claim 37, column 16, line 4, following "metal" and before "said", please delete "as" and insert therefor --on--.

Signed and Sealed this

Thirteenth Day of January, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,627,125

DATED : May 6, 1997

INVENTOR(S) : Jerry R. Ebner and Thaddeus S. Franczyk

Figure 2:
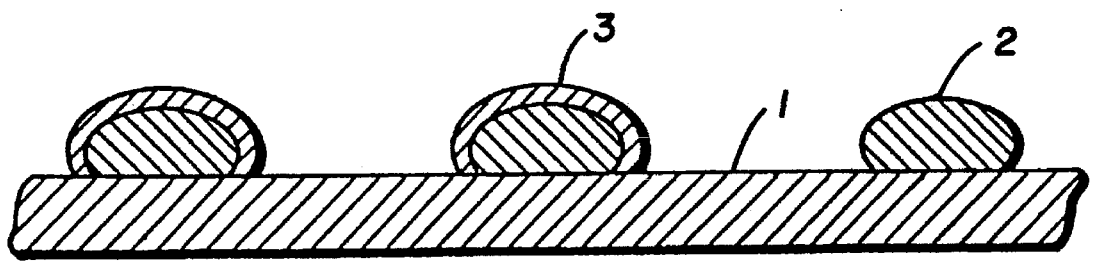
In FIG. 2 one particle of anchor metal 2 is illustrated as having not been electrolessly plated. A particle of the nonprecious metal which is attached to the support but which has not been plated on the anchor metal is denoted by numeral 4.

It is certified that error appears in the above-identified patent and that said Letters Patent is hereby corrected as shown below:

In the drawings, please delete Fig. 2. and insert therefor

--

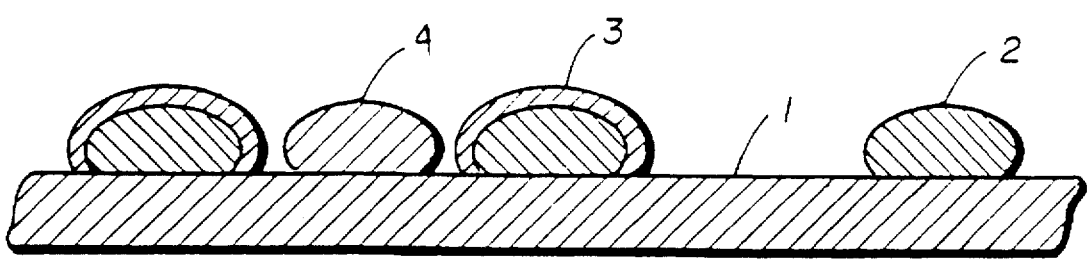

FIG. 2.

--